US012691201B2

(12) United States Patent
Schouenborg

(10) Patent No.: US 12,691,201 B2
(45) Date of Patent: Jul. 28, 2026

(54) METHOD OF PROVIDING AN IMPLANTATION SITE IN SOFT TISSUE

(71) Applicant: NEURONANO AB, Karlshamn (SE)

(72) Inventor: Jens Schouenborg, Lund (SE)

(73) Assignee: NEURONANO AB (SE)

( * ) Notice: Subject to any disclaimer, the term of this patent is extended or adjusted under 35 U.S.C. 154(b) by 0 days.

(21) Appl. No.: 18/230,404

(22) Filed: Aug. 4, 2023

(65) Prior Publication Data

US 2023/0405181 A1 Dec. 21, 2023

Related U.S. Application Data

(63) Continuation of application No. 16/073,365, filed as application No. PCT/SE2017/000013 on Feb. 23, 2017, now abandoned.

(30) Foreign Application Priority Data

Feb. 26, 2016 (SE) .................................. 1600069-7

(51) Int. Cl.
*A61N 1/05* (2006.01)
*A61B 5/00* (2006.01)
(Continued)

(52) U.S. Cl.
CPC .......... *A61L 27/222* (2013.01); *A61B 5/0084* (2013.01); *A61B 5/686* (2013.01);
(Continued)

(58) Field of Classification Search
CPC .......... A61B 17/3468; A61B 2090/306; A61B 5/0084; A61B 5/686; A61B 90/10; A61B
2560/063; A61B 2562/0209; A61B 2562/028; A61B 2562/14; A61B 2562/146; A61L 27/222; A61L 2400/04; A61L 2400/06; A61N 1/0551; A61M 25/007

See application file for complete search history.

(56) References Cited

U.S. PATENT DOCUMENTS 3,810,471 A 5/1974 Truhan
4,402,684 A 9/1983 Jessup
(Continued)

FOREIGN PATENT DOCUMENTS

WO 2007/028003 A2 3/2007
WO 2009/075625 A1 6/2009
(Continued)

OTHER PUBLICATIONS

International Search Report mailed May 23, 2017 in corresponding PCT International Application No. PCT/SE2017/000013.
(Continued)

*Primary Examiner* — Jing Rui Ou
(74) *Attorney, Agent, or Firm* — OSTROLENK FABER LLP

(57) ABSTRACT

A method of providing a channel filled with aqueous gel in soft tissue comprises injecting a biocompatible aqueous gel into the tissue. Also disclosed is a corresponding device, the combination of the device and a guide for its insertion into tissue, and a system comprising the combination and a reservoir filled with aqueous gel comprising means for exerting pressure on the gel.

19 Claims, 4 Drawing Sheets

(51) Int. Cl.

| | |
|---|---|
| *A61B 17/34* | (2006.01) |
| *A61L 27/22* | (2006.01) |
| *A61M 25/00* | (2006.01) |
| *A61B 90/10* | (2016.01) |
| *A61B 90/30* | (2016.01) |

(52) U.S. Cl.
CPC ........ *A61B 17/3468* (2013.01); *A61N 1/0551* (2013.01); *A61B 90/10* (2016.02); *A61B 2090/306* (2016.02); *A61B 2560/063* (2013.01); *A61B 2562/0209* (2013.01); *A61B 2562/028* (2013.01); *A61B 2562/14* (2013.01); *A61B 2562/146* (2013.01); *A61L 2400/04* (2013.01); *A61L 2400/06* (2013.01); *A61M 25/007* (2013.01)

(56) References Cited

U.S. PATENT DOCUMENTS

| | | | |
|---|---|---|---|
| 5,425,723 A | 6/1995 | Wang | |
| 5,536,261 A | 7/1996 | Stevens | |
| 5,605,537 A | 2/1997 | Ivey | |
| 5,800,408 A | 9/1998 | Strauss | |
| 6,205,359 B1 | 3/2001 | Boveja | 607/45 |
| 7,004,923 B2 | 2/2006 | Deniega | |
| 2003/0050683 A1 | 3/2003 | Boutos | |
| 2007/0135881 A1 | 6/2007 | Vilims | 607/117 |
| 2007/0213688 A1 | 9/2007 | Klein | |
| 2007/0260250 A1 | 11/2007 | Wisnewski | |
| 2009/0112273 A1 | 4/2009 | Wingeier et al. | 607/3 |
| 2009/0112278 A1 | 4/2009 | Wingeier et al. | 607/45 |
| 2009/0312744 A1 * | 12/2009 | Keeley | A61M 5/142 604/506 |
| 2010/0111829 A1 * | 5/2010 | Drapeau | A61K 47/34 424/1.11 |
| 2010/0215715 A1 * | 8/2010 | Han | A61P 19/00 424/423 |
| 2011/0060373 A1 | 3/2011 | Russell | |
| 2011/0087315 A1 | 4/2011 | Richardson-Burns et al. | 607/116 |
| 2011/0295262 A1 * | 12/2011 | Germain | A61B 17/1642 606/84 |
| 2012/0041394 A1 * | 2/2012 | Haider | A61M 25/0068 604/272 |
| 2012/0078330 A1 | 3/2012 | Doerr | 607/116 |
| 2014/0121587 A1 | 5/2014 | Sallberg et al. | 604/21 |

FOREIGN PATENT DOCUMENTS

| | | | |
|---|---|---|---|
| WO | 2010/054308 A1 | 5/2010 | |
| WO | 2011/004971 A2 | 1/2011 | |
| WO | 2013/191612 A1 | 12/2013 | |
| WO | 2016/032384 A1 | 3/2016 | |

OTHER PUBLICATIONS

Written Opinion mailed May 23, 2017 in corresponding PCT International Application No. PCT/SE2017/000013.

G. Lind et al., "Gelatine-embedded electrodes—a novel biocompatible vehicle allowing implantation of highly flexible microelectrodes," Journal of Neural Engineering, vol. 7, 10 pages (2010).

G. Lind et al., "The density difference between tissue and neural probes is a key factor for glial scarring," Journal of Scientific Reports, vol. 3, 7 pages (2013).

* cited by examiner

METHOD OF PROVIDING AN IMPLANTATION SITE IN SOFT TISSUE

CROSS REFERENCE OF RELATED PATENT APPLICATION

This is a continuation of prior application Ser. No. 16/073, 365, filed Jul. 27, 2018, by Jens SCHOUENBORG entitled METHOD OF PROVIDING AN IMPLANTATION SITE IN SOFT TISSUE, which is a 35 U.S.C. §§ 371 national phase application of PCT/SE2017/000013, filed Feb. 23, 2017, which claims priority of Swedish Patent Application No. 1600069-7, filed Feb. 26, 2016, the contents of which are incorporated by reference herein. The PCT International Application was published in the English language.

BACKGROUND OF THE INVENTION

The present invention relates to a method of providing an implantation site in soft tissue, in particular in nervous tissue, and to a corresponding means.

The object to be implanted can be medical device or other object that is not sufficiently physically stable for direct implantation by insertion into the tissue. In particular, the medical device of the invention is a microelectrode or a microprobe such as an electrical or optical sensor. The object to be implanted can also be a living cells such as cultured cells, in particular stem cells, as well as cell aggregates and pieces of living tissue.

Implantation of living cells, such as stem cells, cell aggregates and tiny pieces of tissue obtained by culturing stem cells and other cells into soft tissue, in particular nervous tissue, is problematic. Single cells are at great risk of be damaged during implantation whereas cell aggregates or tissue fragments are at risk of being disintegrated. Another problem consists in how to dispose cells or cell aggregates at a desired tissue location. An additional problem is nervous tissue irritation by foreign material resulting in loss of neurons and proliferation of astrocytes. To maintain the integrity of an aggregate of cells or a tissue fragment during implantation they need to be physically protected. The use of physical protection means for their implantation into soft tissue risks to elicit a negative response of the tissue into which they are implanted so as to jeopardize survival and integration.

Implantation of tiny microelectrodes and optical fibers is often jeopardized by their fragmentation during insertion into soft tissue. In the art this problem is solved by enclosing the electrode body or at least a portion thereof extending from its distal end or tip in a proximal direction with a stiff matrix, which is dissolved or degrades by aqueous nervous or body fluid at a rate substantially lower than the rate of insertion. Physically insufficiently stable devices for implantation into soft tissue furthermore comprise sensors of various kind, such as glucose sensors, which can be used for controlling administration of insulin, and radiative sensors comprising optical fibers.

The high local concentration of matrix fragments caused by dissolution or degradation is problematic. It changes temporarily the natural environment of a targeted nerve cell or a group of nerve cells, and thereby affects their behavior until matrix solutes have been transported away from the site of insertion. The removal of matrix solutes from the site of insertion by convection or diffusion is time consuming. Until all or practically all such solutes have been removed the electrode cannot be used or can only be used for monitoring a nerve cell or a group of nerve cells under the influence of such solutes. Single electrodes and groups of electrodes comprising a tiny oblong metallic electrode body enclosed by a biodissolvable or biodegradable matrix are disclosed in, for instance, WO 2009/075625 A1.

Another problem is that, in order to being sufficiently rigid for insertion into tissue, the matrix need to be of a radial dimension substantially larger than that of the electrode body. This requirement may result in electrode body/matrix combinations of a radial dimension causing substantial injury to the tissue into which the combination is inserted.

Still another problem is that, due to variation in functional organization and anatomy of tissue, in particular brain tissue, between subjects, optimal placement of microelectrodes in the tissue may require repetitive insertion and evaluation of the corresponding disposition. Matrix covered microelectrodes of the art are not well adapted to repetitive insertion since they will lose some of their matrix material in each insertion and, at worst, will lose so much thereof that their rigidity will be compromised before a desired disposition in the tissue can be obtained. This may be accompanied by loss of pharmaceutical(s) or biological material incorporated in their matrix, which material may negatively affect the tissue of interest.

An additional problem or limitation of matrix covered microelectrodes resides in their limited rate of insertion into soft tissue: to avoid excessive tissue injury the microelectrodes have to be inserted rather slowly. The more slowly they are inserted the higher is the risk of matrix material and, if present, pharmaceutical(s) or other agents incorporated into the matrix being lost during insertion on the way and not reaching the desired disposition for release. This problem is particularly evident with probes comprising frozen biological material.

A further problem with the insertion of matrix-covered microelectrodes of the art is bleeding of the wound caused by the microelectrode. This may lead to local coagulated blood sticking to the matrix surface will substantially delay the dissolution or degradation thereof, and thereby the use of the microelectrode for the intended purpose.

An additional important problem is nervous tissue irritation caused by the implants such as microelectrodes resulting in loss of neurons and proliferation of astrocytes (Lind G et al., J Scientific Reports 3 (2013); article no. 2942DOI: doi:10.1038/srep02942).

Gelatin-embedded electrodes implanted in brain tissue are disclosed in G Lind et al., J Neural Eng 7 (2010) 046005 (doi:10.1088/1741-2560/7/4/046005). Gelatin-embedded metal microelectrodes or bundles of microelectrodes implanted into the brain show improved functionality over extended periods of time accompanied by reduced acute tissue reactions.

OBJECTS OF THE INVENTION

A primary object of the invention is to provide a method of the aforementioned kind that solves one or several problems related to the insertion of known microelectrodes and other objects into neural tissue. Neural tissue comprises brain and spinal cord tissue but also peripheral nerves, dorsal root ganglia, and retina tissue.

Other objects of the invention are to prevent or reduce or stop bleeding along a neural tissue insertion path for a medical device or other object such as an aggregate of cells or a tissue fragment; to protect neighboring nerve cells from negative effects of such implantation; to the preservation of the capacity of correcting the disposition of implanted microelectrodes and other objects;

Another object of the invention is to provide an apparatus for use in the method. A further object of the invention is to provide a method of manufacture of the apparatus.

Additional objects of the invention will become apparent from the following summary of the invention, the description of preferred embodiments thereof illustrated in a drawing, and from the appended claims.

SUMMARY OF THE INVENTION

The present invention is based on the insight that the provision of a channel in neural tissue filled with a biocompatible aqueous gel such as aqueous gelatin gel allows implantation by insertion into neural tissue of medical devices or other objects that are insufficiently physically stable for direct insertion into neural tissue. Neural tissue comprises brain and spinal cord tissue.

The channel of the invention is preferably rotationally symmetric, more preferred cylindrical and has a corresponding central, longitudinally extending axis. The channel of the invention is preferably straight or substantially straight, that is, linear or substantially linear. Substantially linear/straight means that when its one end is disposed on the central axis a straight line passing through its other end forms an angle with the central axis of not more than 10° with the axis, preferably of not more than 5°. The channel of the invention has a length substantially greater than its width, in particular by a factor of 5 or 10 or 20 and more. The side and bottom (front) walls of the channel are formed by living nervous tissue. For this and other reasons the geometry of the channel may change over time. In particular, the diameter of the channel may shrink over time.

The biocompatible gel prevents shrinkage of the channel radially inwardly and thus stabilizes the geometry of the channel, at least for a period of time during which the gel is not substantially altered, that is, weakened by enzymatic degradation or otherwise. The use of cross-linked gels may extend the time of substantially stabilized geometry, which can be tailored by the extent of crosslinking.

The biocompatible gel allows tiny structures like thin filaments or electrodes or optical fibers to be inserted into it, in particular slowly inserted into it, without substantially affecting their geometry. A slow rate of insertion is a rate of up to 5 mm per second, in particular of 1 or 2 mm per second. This is in stark contrast to the resistance of soft tissue, in particular nervous tissue, to such insertion. Typically, the resistance of an aqueous gel of the invention is lower by a factor of 10 or more, in particular by a factor of 25 or more than the resistance of neural tissue, in particular the meninges and other fibrous membrane layers. A measure of the resistance against penetration is the time required for an oblong pin of given dimensions to penetrate to a defined depth under the influence of a constant force acting on the pin in an axial distal direction.

The biocompatible gel is translucent, which is particularly advantageous for the use of visible and near IR radiation emitted through an optical fiber disposed in the channel.

The present invention is also based on the insight that insertion of matrix stabilized microelectrodes or probes of the art can be improved by the method of the invention. The provision of a channel of the aforementioned kind may reduce, even substantially reduce, the amount of matrix material dissolvable or degradable by body fluid required for their stabilization during insertion into soft tissue.

The channel of the invention is formed in situ by introducing a biocompatible aqueous gel into soft tissue. An important feature of the invention is that the biocompatible aqueous gel is introduced into the tissue as such, not in the form of a precursor forming a gel in the tissue in contact with aqueous body fluid.

Introduction of the biocompatible aqueous gel into soft tissue is accomplished by injecting it by means of a device inserted into the tissue upon or during insertion of the device into the tissue.

According to the present invention is disclosed a device of this kind in form of an elongate rotationally symmetric rigid pin comprising a central axially extending passage and lateral passages extending radially from the central passage and penetrating the tube wall. The passage is closed at its distal end and open at its proximal end. The pin comprises a central section provided with said axially extending passages and distal and proximal sections lacking such passages. The diameter of the distal section narrows towards its distal end so as to form a sharp or blunt tip that facilitates insertion into the tissue. A flexible tube is mounted the frontal end of the pin in communication with the passage and, at its other end, with a reservoir for biocompatible aqueous gel. The reservoir can be loaded with aqueous gel, in particular via a releaseable loading closure. Alternatively the device of the invention can be provided in a loaded state, either with its reservoir loaded or with both its reservoir and its channels loaded with aqueous gel. A device loaded in this manner can be protected by a removable foil covering the outer openings of the radially extending channels. The reservoir is adapted to allow aqueous gel being expelled from it by a pump or by handicraft, in which case a wall of the reservoir is of a flexible material, for instance in form of a balloon. The device as well as the aqueous gel are provided in a sterile state.

The pin can comprise or consist of a metal or a metal alloy, preferred metals being selected from the group consisting of gold, silver, copper, platinum, iridium, titanium, chromium, tungsten, aluminum and their alloys, any of tungsten, iridium and stainless steel being particularly preferred. Alternatively the pin can be of a stiff polymer material such as, for instance, polyacrylate and polycarbonate.

The pin may also comprise an electrode or an optical fiber of which the detection end is disposed at a distal terminal face of the pin.

In the method of the invention the device is partially inserted into the tissue with its front end foremost to a minimum depth corresponding to the combined axial extension of said distal and central sections or to a greater depth. During insertion and/or upon insertion pressure is applied to the aqueous gel in the reservoir and the passages, whereby aqueous gel is pressed out from the outer openings of the radially extending channels, forcing tissue abutting the outer face of the central section away from the pin so as to form a layer of aqueous gel around the central section. Withdrawal of the pin from the tissue leaves a channel in the tissue filled with the gel.

According to a preferred embodiment the device of the invention is positionally stabilized, that is, stabilized against disposition in a radial direction, during insertion into tissue and expulsion of aqueous gel from it by a tubiform insertion guide into the lumen of which the pin is insertable. The radial diameter of the lumen is slightly larger than the radial width of the pin so as to allow the pin to be slidingly displaced within the insertion tube. According to an advantageous aspect of the invention the insertion tube is of a minimum length corresponding to the axial length of said central section provided with radial conduits. According to a further advantageous aspect of the invention the insertion guide comprises a radially extending flange mounted at its distal end. The width of the flange is preferably greater, more preferred substantially greater such as by at least 20% or 50% than the width of a channel filled with aqueous gel produced by means of the device of the invention stabilized in such manner. According to a still further advantageous aspect of the invention the insertion guide is secured in an insertion position in which it abuts the surface of the tissue in which the channel of the invention is desired to be provided, the insertion guide being centered so as to make its center coincide with the imaginary center of the channel. This is achieved by immobilizing the insertion guide in a thus selected position by firmly connecting it, directly or indirectly with the immobilized person or animal of which a tissue is to be provided with a channel of the invention via a holding element comprised by the guide and firmly mounted at the tubiform portion and/or the flange thereof. Thus, according to the present invention is disclosed the combination of the device and the insertion guide.

A preferred aspect of the present invention is based on the additional insight that the formation of aqueous biocompatible gel, in particular of aqueous gelatin gel, in the channel can have neuroprotective effect comprising reduction of microglia response to medical devices implanted into neural tissue.

A particularly preferred aqueous gel is gelatin gel. According to the present invention gelatin from various animal sources can be used as a gel forming agent, such as bovine, pig skin, poultry skin, and tuna gelatin. Gelatin from mammal sources is preferred due to its superior gelling capacity at body temperature. For forming a channel of extended stability the use of chemically cross-linked gelatin is preferred due to its slower rate of degradation in the body. Examples of efficient gelatin cross linking agents are bis (vinylsulfonyl)methane and 1-ethyl-3(3-dimethylamino-propyl)carbodiimide. Another useful crosslinking method is by UV radiation. The rate of degradation in the body can be controlled by the extent of cross-linking, which in turn can be controlled by the amount of cross-linking agent used or by controlling the exposure to UV radiation used for cross-linking a given amount of gelatin. Another useful gelatin gel is based on recombinant gelatin.

Other aqueous biocompatible gels of the invention include carbohydrate gels. Carbohydrate gels useful in the invention include arabinogalactan gel, arabinoxylan gel, galactan gel, galactomannan gel, lichenan gel, xylan gel but also cellulose derivatives such as hydroxymethylpropyl cellulose, and are formed by contact with aqueous media, in particular aqueous body fluid, with a gel forming agent selected from: arabinogalactan, arabinoxylan, galactan, galactomannan, lichenan, xylan, hydroxymethyl cellulose and other cellulose derivatives forming gels in contact with aqueous media.

Further aqueous biocompatible gels of the invention include protein gels. Protein gels other than gelatin from animal sources useful in the invention include whey protein gel, soy protein gel, casein gel, which are formed by contact of aqueous media, in particular aqueous body fluid with a gel forming agent selected from whey protein, soy protein, casein.

Still other aqueous gels for use in the invention can be formed by contact of aqueous media, in particular aqueous body fluid, with a gel forming agent selected from the group consisting of: arabinogalactan; arabinoxylan; galactan;

galactomannan; lichenan; xylan; cellulose derivatives such as hydroxymethylpropyl cellulose; whey protein; soy protein; casein; hyaluronic acid; chitosan; gum Arabic; carboxyvinyl polymer; sodium polyacrylate; carboxymethyl cellulose; sodium carboxymethyl cellulose; pullulan; polyvinylpyrrolidone; karaya gum; pectin; xanthane gum; tragacanth; alginic acid; polyoxymethylene; polyimide; polyether; chitin; poly-glycolic acid; poly-lactic acid; copolymer of poly-glycolic and poly-lactic acid; co-polymer of poly-lactic acid and polyethylene oxide; polyamide; polyanhydride; polycaprolactone; maleic anhydride copolymer; poly-hydroxybutyrate co-polymer; poly(1,3-bis(p-carbophenoxy)propane anhydride); polymer formed by co-polymerization with sebacic acid or with poly-terephthalic acid; poly(glycolide-co-trimethylene carbonate); polyethylene glycol; polydioxanone; polypropylene fumarate; poly(ethyl glutamate-co-glutamic acid); poly(tert-butyloxy carbonylmethyl glutamate); poly-caprolactone; poly(caprolactone-co-butylacrylate); poly-hydroxybutyrate and copolymers thereof; poly(phosphazene); poly(D,L-lactide-co-caprolactone); poly(glycolide-co-caprolactone); poly(phosphate ester); poly(amino acid); poly(hydroxybutyrate); polydepsidpeptide; maleic anhydride copolymer; polyphosphazene; polyiminocarbonate; poly[(7.5% dimethyl-trimethylene carbonate)-co-(2.5% trimethylene carbonate)]; polyethylene oxide; hydroxypropylmethylcellulose, poly(ethylene-co-vinyl acetate); isobutylene-based copolymer of isobutylene and at least one other repeating unit such as butyl acrylate: butyl methacrylate; substituted styrene such as amino styrene, hydroxy styrene, carboxy styrene, sulfonated styrene; homopolymer of polyvinyl alcohol; co-polymer of polyvinyl alcohol and at least one other repeating unit such as a vinyl cyclohexyl ether; hydroxymethyl methacrylate; hydroxyl- or amino-terminated polyethylene glycol; acrylate-based copolymer such as methacrylic acid, methacrylamide, hydroxymethyl methacrylate; ethylene vinyl alcohol copolymer; silicone based copolymer of aryl or alkyl siloxane and at least one repeating unit; polyurethane; heparan sulfate; RGD peptide; polyethylene oxide; chrondroitin sulfate; YIGSR peptides; keratan sulfate; VEGF biomimetic peptide; perlecan (heparan sulfate proteoglycan 2); Ile-Lys-Val-Ala-Val (IKVAV) containing laminin alpha-1 chain peptide; modified heparin; fibrin fragments.

According to a further aspect of the invention is provided a system for providing a channel in soft tissue filled with aqueous gel, the system comprising a combination of the device of the invention, an insertion guide, a reservoir filled with aqueous gel in fluid communication with the device, and a means for applying pressure to the gel in the reservoir.

The invention will now be explained in more detail by reference to a number of preferred embodiments illustrated in a rough drawing. For reasons of clarity the drawing is not to scale. In particular, radial dimensions are often exaggerated in respect of axial dimensions.

BRIEF DESCRIPTION OF THE DRAWING(S)

Figures 2A, 2B:
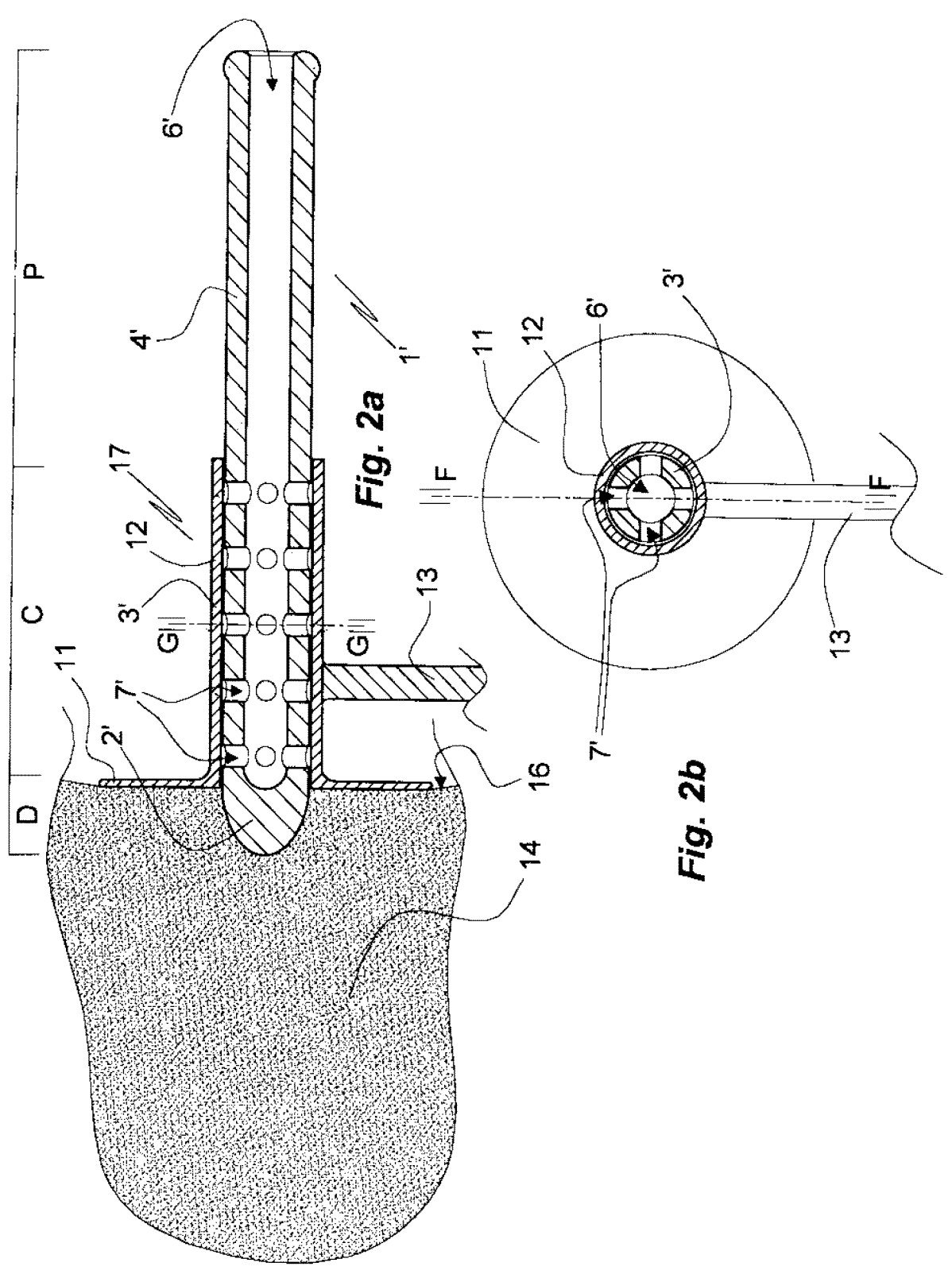
FIGS. 2a, 2b are axial F-F and radial G-G sections of a second embodiment of the device of the invention.

FIG. 2c— 2f in combination with FIGS. 2a, 2b illustrate the formation of a channel in soft tissue filled with aqueous gel by disposing a device of the invention at the tissue surface and securing it in the selected position by means of an insertion guide, in an axial view and a radial view (FIG. 2b).

DESCRIPTION OF PREFERRED EMBODIMENTS

Example 1. First Embodiment of the Device of the Invention

The device 1 of the invention has the form of an oblong cylindrical (central axis B-B) hollow pin 1. The pin is substantially rigid and made of a suitable material, such as a metal or a polymer. An axial passage or bore 6 in the pin 1 extends from its open proximal end 4' to near its distal end 2' at which the passage 6 is closed. The 1 pin comprises a central section C provided with constant radius, disposed between a distal section D with a radius decreasing towards the distal end 2' and a proximal section P comprising an annular bulge 5 for attaching a flexible tube 8. The central section C is provided with radially extending bores 7 communicating with the central passage 6 and opening at the cylindrical outer face of the pin 1. Sets of bores each comprising four are arranged at regular axial distance intervals in a radial plane. The illustrated arrangement of radially extending bores is not critical, the important feature being that sufficient bores of this kind are provided over the entire central section. The axial extension of the central section C corresponds roughly to the depth of a channel in soft tissue filled with aqueous gel provided by means of the pin 1. Near the proximal end the holding element 10 is fastened to the proximal section P of the pin 1 by means of an annular clamp 9. The holding element 10 extends from the annular clamp 9 in a radial direction; its other end (not shown) is firmly connected, directly or indirectly, to the person or animal in a soft tissue of which a channel of the invention is intended to be provided. By indirectly is meant, for instance, fixation to a support on which the person or animal rest during the channel forming procedure.

Example 2. Second Embodiment of the Device of the Invention

The second embodiment of the device 1' of the invention in form of a pin 1' shown in FIGS. 2a, 2b in axial (D-D) and radial (E-E) sections differs from the first embodiment by omission of holding element 10 fastened at the proximal section P of the pin 1 by means of the annular claim 9 and by the axial length of the proximal section P exceeding the axial length of the central section C. While the second embodiment is provided at its proximal end with a flexible tube corresponding to the tube 8 of the first embodiment, the tube is not shown in FIGS. 2a-2b for reasons of drawing space economy. Reference numbers 2', 3', 4', 6' as well as reference letters D', C', P' correspond to respective features 2, 3, 4, 6, D, C, P of the first embodiment.

Figures 2C, 2D:
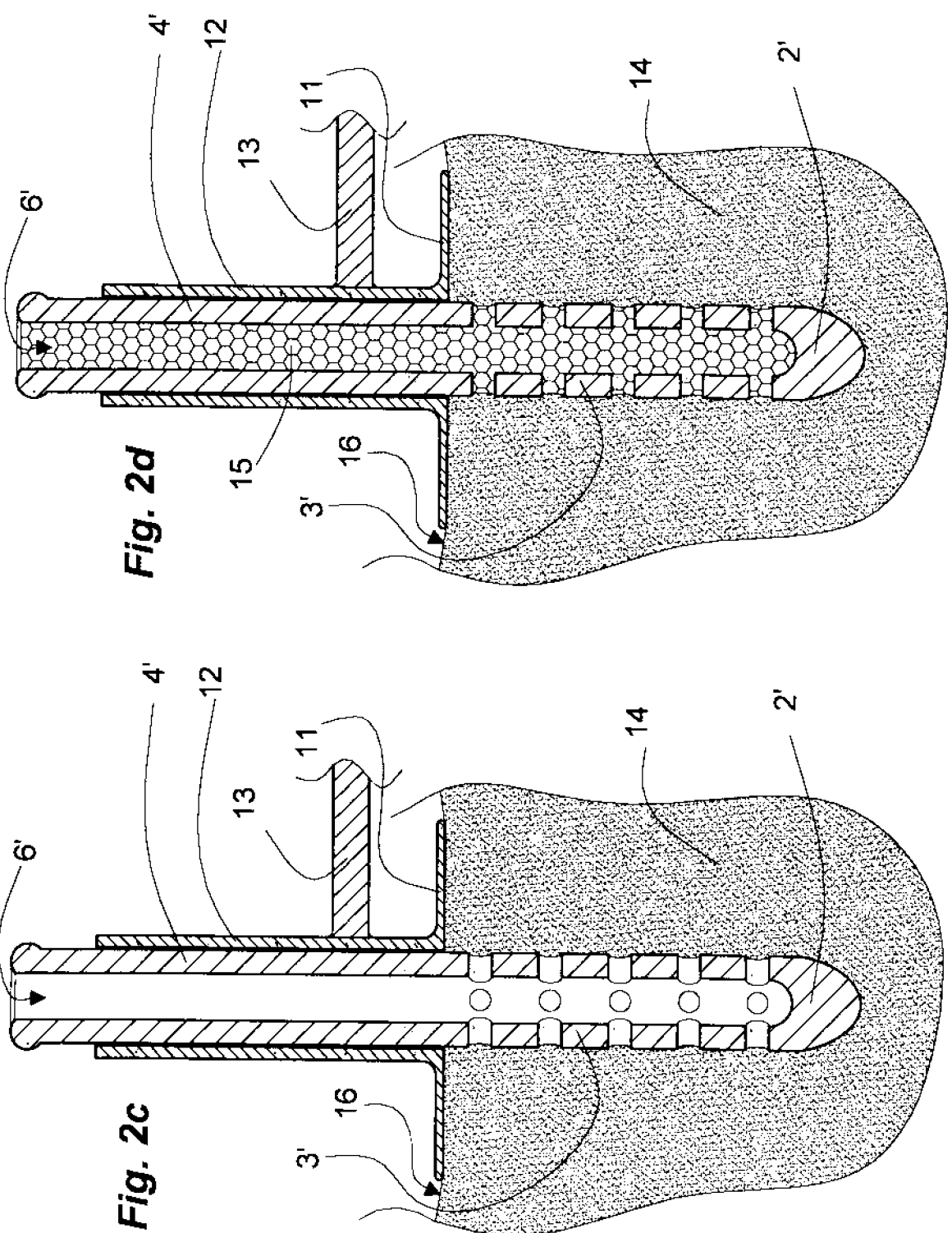

In FIGS. 2a, 2c and 2d the pin 1' is mounted at the site for its insertion into soft tissue 14 by means of insertion guide 17 comprising a sleeve 12 into the lumen of which the pin 1' can be inserted. The radial diameter of the sleeve 12 lumen is slightly larger than the radial width of the pin 1' so as to allow the pin 1' to be slidingly displaced within the sleeve 12. According to an advantageous aspect of the invention the axial length of the sleeve 12 is somewhat greater than the axial length of the central section C' section provided with radial conduits 7'. According to a further advantageous aspect of the invention the insertion guide 17 comprises a radially extending flange 11 mounted at the distal end of the sleeve 12. The width of the flange 11 is substantially greater than the width of a channel filled with aqueous gel 15 produced by means of the device 1' of the invention. The insertion guide 17 is secured in an insertion position in which its flange 11 abuts the surface 16 of the tissue 14 in which the channel of the invention is desired to be provided, the insertion guide 17 being centered so as to make its center coincide with the imaginary center of the channel. This is achieved by immobilizing the insertion guide 17 in a so selected position by firmly connecting it, directly or indirectly with the immobilized The channel 6' is in communication person or animal of which a tissue 14 is to be provided with a channel of the invention filled with aqueous gel 15 via a holding element 13 comprised by the insertion guide 17 and firmly mounted at its sleeve 12 and/or the flange 11 thereof. By a flexible tube (not shown) attached to the proximal end of the pin 1' the channel is in fluid communication with a reservoir (not shown) holding aqueous gelatin gel.

Example 3. Third Embodiment of the Device of the Invention

Figures 1, 1A, 1B:
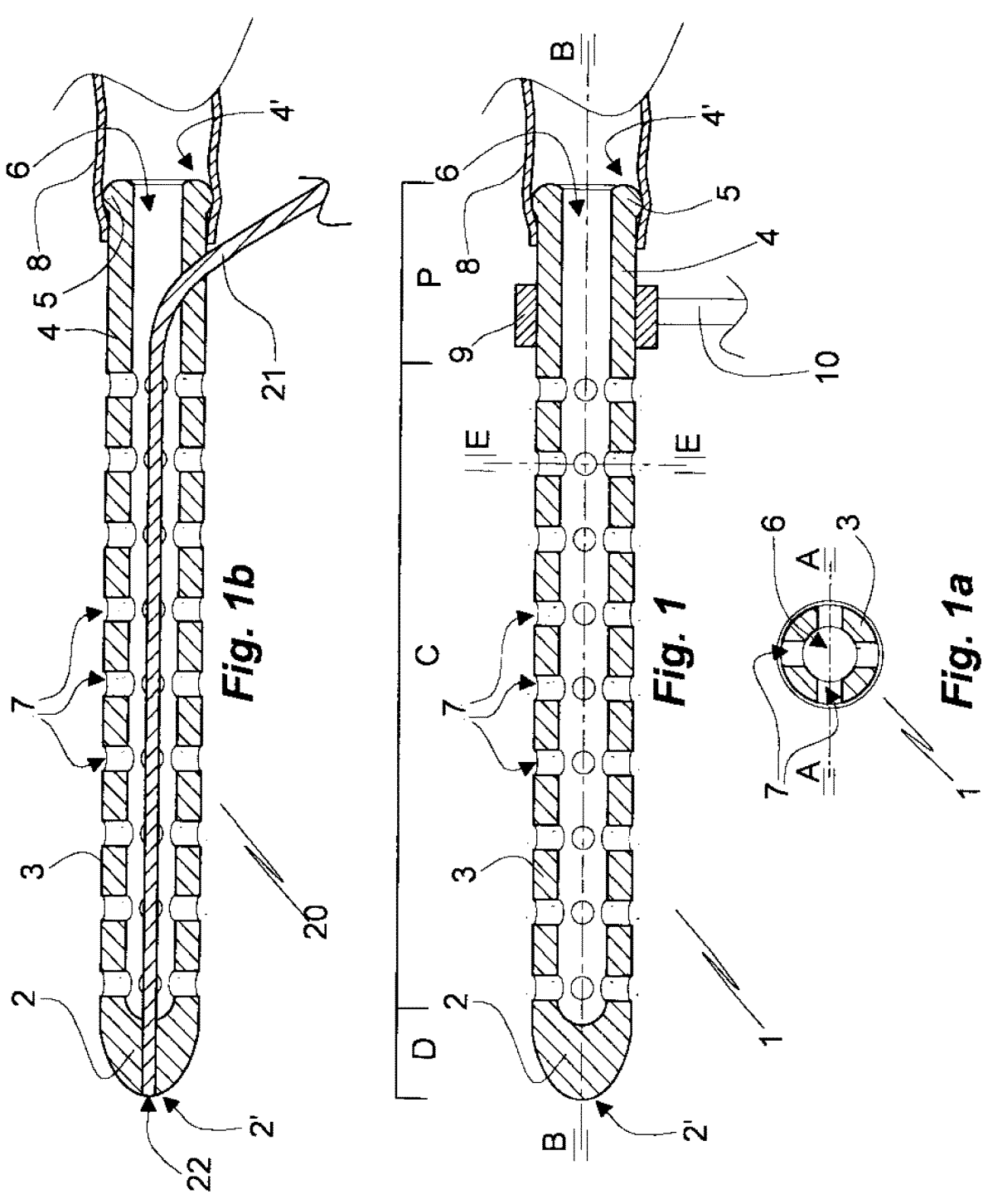
FIGS. 1 and 1a are axial (A-A) and radial (E-E) sections of a first embodiment of the device of the invention.
FIG. 1b is an axial section of a third embodiment of the device of the Invention, in the same axial section as the device of FIG. 1.

The second embodiment 20 of the device of the invention in form of a pin 20 shown in FIG. 1b in an axial section corresponds generally to the pin 1 of FIG. 1 from which it differs by omission of the annular clamp 9 and the holding element 10 and by comprising a conductor 21 which is an electrode 21 or optical fiber 21 disposed centrally in the conduit 6. At its distal detection end 22 the electrode or fiber 21 is embedded in the distal portion P of the pin 20 in a manner that its distal face 22 forms a central section of the face of distal portion P at the distal end 2' of the pin 20. Except for at its distal end 2' the electrode 21 is insulated (not shown). The conductor leaves the conduit 6 laterally near the lateral end 4' thereof.

The electrode 21 or optical fiber 21 can be used, for instance, for assisting in guiding insertion of the pin 20 to a desired depth by optically or electrically detecting a structure in the tissue, for instance a nerve cell, in the vicinity of which the front end of the channel filled with aqueous gel of the invention is desired to be located.

Example 4. Provision of a Channel of the Invention in Soft Tissue Filled with Aqueous Gel The process of providing a channel of the invention in soft tissue 14 filled with aqueous gel 15 is shown in FIGS. 2a, 2c, 2d.

In the state of FIG. 2a the sleeve 12 fully covers the radially extending bores 7' of the central section C; pressure exerted on the aqueous gel in the reservoir, for instance by compression of the reservoir if comprising a flexible wall, results in the gel filling the central passage 6' and the radially extending bores 7' but not escaping from there due to the high viscosity of the gel. On the other hand, air or other gas present in the central passage 6' and the radial bores 7' can escape through the radial bores 7' since the sleeve 12 does not completely seal them. Thereby the state shown in FIG. 2b is reached.

In the next step the pin 1' is inserted fully into the tissue 14, that is, to a desired position. The state reached by the insertion is shown in FIG. 2c by insertion during no pressure is exerted on the aqueous gel. Alternatively a slight or a high pressure is exerted on the aqueous gel during insertion, which makes aqueous gel escape from bores 7'. While the application of a slight pressure is beneficial for insertion due to the escaped gel functioning as a glidant and protecting the tissue from mechanical damage by the pin 1', the application of a high pressure is not beneficial since gel may easily escape from the channel being formed. It should also be kept in mind that forcing the gel to pass through narrow conduits affects its rheological properties so as to temporarily reduce gel strength.

By increasing the pressure on the gel in the reservoir gel 15 is forced out from the bores 7' forming a cylinder of gel 15 around the central portion C of the pin and an adjacent part of the distal portion D (FIG. 2d).

Figures 2E, 2F:
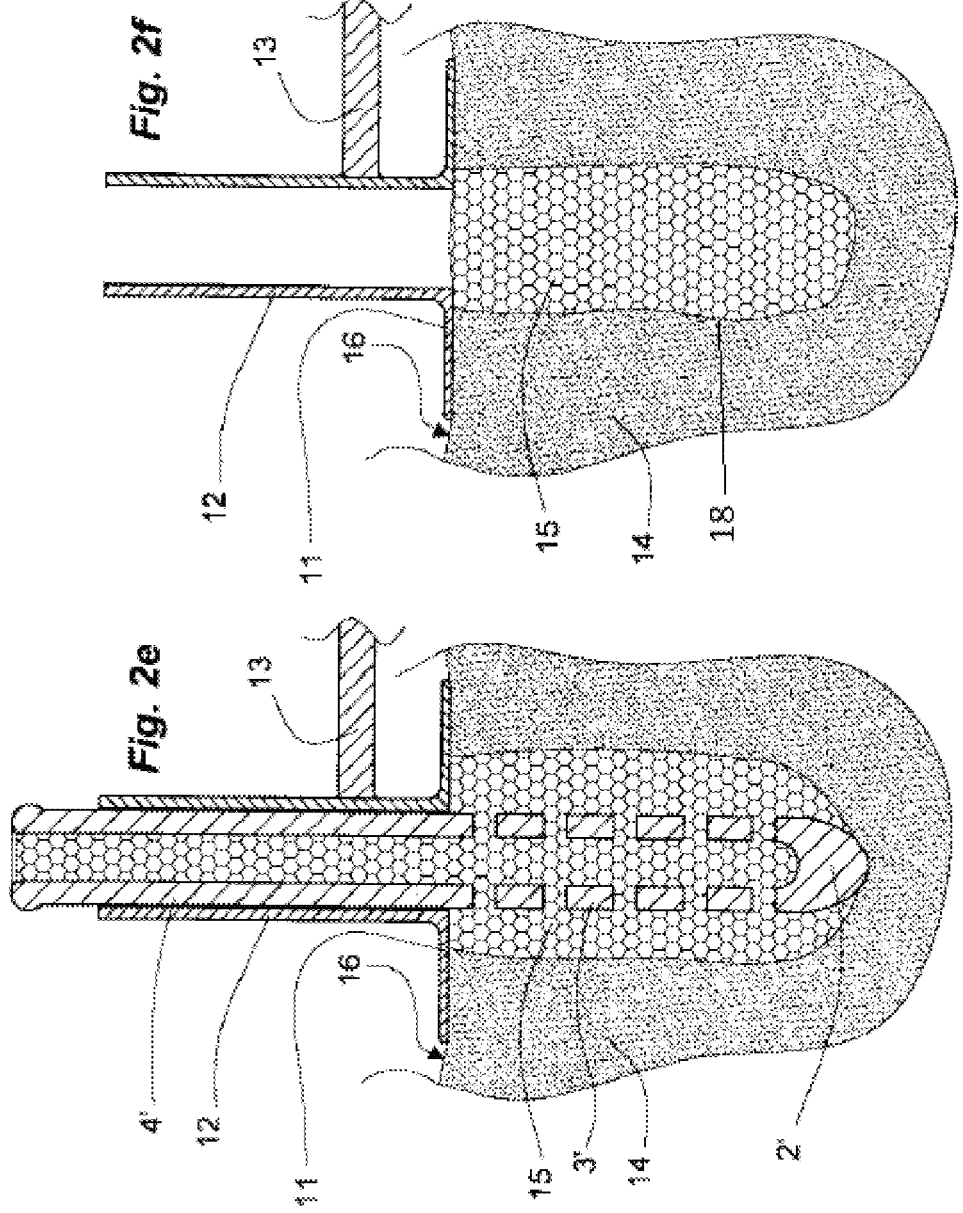

Withdrawal of the pin 1' from the cylinder of gel 15 makes the gel 15 shrink due to pressure from surrounding tissue 14 to form the channel 18 of the invention filled with aqueous gel 15 (FIG. 2e). Prior to withdrawal of the pin 1', in particular prior to insertion of a device of a rigidity which does not allow direct insertion into soft tissue the gel 15 in the channel 18 should be given time to fully stabilize. The time required for stabilization of different kinds of gels has to be experimentally determined.

Upon withdrawal of the pin 1' the insertion guide 17 can be left mounted at the channel 18 site for protecting the channel until it is used for implantation; in such case its distal opening has to be provided with a closure. Alternatively and additionally, the insertion guide 17 can be used as a guide for a syringe or pipette or other instrument for injection or insertion of a microelectrode, an optical fiber, a suspension or aggregate of living cells, a tissue fragment, a pharmaceutical, etc. into the channel 18.

Example 4. Manufacture of the Device of the Invention

Pins of the invention are preferably manufactured in two halves. The axial section of FIG. 1 can be taken to represent one such half if considered to be a side view rather than a section. Halves of non-resilient metal can be made by pressure forming thin metal sheet in a mould. The halves can be united by welding or soldering. Halves of a polymer can be produced by, for instance, injection moulding and be united in consideration of the particular polymer properties, such as by fusing them together at their meeting faces or by adhesive means. Suitable polymers include but are not restricted to PVC, polyacrylate, polycarbonate and polystyrene. The manufacture of the insertion guide is trivial and need not be commented on.

What is claimed is:

1. A method for forming, with a device, a substantially straight channel filled with aqueous gel in soft tissue, the channel being used for subsequent insertion of structures in the micrometer range such as a thin filament, or an electrode of an optical fiber, the device comprising an oblong, rigid pin comprising a distal section extending from a distal end of the pin towards a proximal end of the pin, a central section extending from the distal section towards the proximal end making up an axial extension, and a proximal section extending from the central section to the proximal end, a central conduit extending from the proximal end to the distal section and closed at its distal end, the distal section having a diameter decreasing towards the distal end forming a sharp or blunt distal end facilitating insertion into the soft tissue, the central conduit providing fluid connection between a reservoir for aqueous gel, the pin in its central section comprising lateral passages extending radially from the central conduit and the lateral passages being distributed over the central section, the channel in the soft tissue that is filled with aqueous gel having a depth corresponding to a length of the pin measured from the distal end of the pin to a proximal end of the central section of the pin, and the distal and proximal sections not having lateral passages extending laterally from the central conduit, the method comprising:

inserting the device into the soft tissue;

supplying the aqueous gel outside of the central section via the central conduit and the lateral passages from the reservoir during insertion of the device by way of applying pressure to the aqueous gel to force neural tissue abutting the outer face of the central section away from the pin to form a layer of aqueous gel around the central section; and withdrawing the device from the tissue while leaving the aqueous gel in the tissue thereby forming the channel filled with the aqueous gel, wherein the gel channel has a configuration enabling the structures to be inserted into the soft tissue without coming in direct contact with the soft tissue.

2. The method of claim 1, wherein the gel is native gelatin, recombinant gelatin, cross-linked gelatin and combinations thereof.

3. The method of claim 1, wherein the gel is carbohydrate or protein gel.

4. The method of claim 3, wherein the carbohydrate gel is selected from the group consisting of arabinogalactan gel, arabinoxylan gel, galactan gel, galactomannan gel, lichenan gel, xylan gel, hydroxymethylpropyl cellulose gel and gels of other gel-forming cellulose derivatives.

5. The method of claim 3, wherein the protein gel is selected from the group consisting of whey protein gel, soy protein gel, casein gel.

6. The method of claim 1, wherein the tissue is nervous tissue.

7. The method of claim 1, wherein the reservoir comprises a compressible reservoir wall and mechanical pump for exerting pressure on the gel.

8. The method of claim 1, wherein the device is mounted at the site selected for forming the channel by means of an insertion guide comprising a tubiform element into which the device is insertable and in which it is displaceable in an axial direction.

9. The method of claim 8, wherein the device is kept in a first position in the tubiform element in which position the outer openings of the lateral passages are closed by the tubiform element.

10. The method of claim 9, wherein the device is kept in a second position in the tubiform element in which a distal and a central portion of the device extends from a distal opening of the tubiform element and in which the outer openings of some or all openings of the lateral passages are not shielded by the tubiform element, which second position is one in which the distal and the central portion of the device is inserted into the soft tissue.

11. The method of claim 1, wherein the distal section of the pin narrows towards the distal end of the pin.

12. The method of claim 11, wherein the pin is cylindrical form, optionally except for at its proximal end.

13. The method of claim 1, wherein the device is of metal and/or polymer.

14. The method of claim 1, wherein the device comprises an electrode or optical fiber.

15. The method of claim 1, wherein the aqueous gel is cross-linked.

16. The method of claim 1, wherein the aqueous gel when pressed out from the openings, forcing the tissue abutting the outer face of the central section away from the pin to form a layer of aqueous gel around the central section.

17. The method of claim 1, wherein the aqueous gel preventing shrinkage of the channel inwardly thereby stabilizing the geometry of the channel.

18. The method of claim 1, wherein the reservoir is disposed at the proximal end of the conduit.

19. The method of claim 1, wherein the lateral passages disposed in the central section are arranged at regular axial distances.

\* \* \* \* \*